United States Patent [19]

Kusuzawa

[11] Patent Number: 5,596,401
[45] Date of Patent: Jan. 21, 1997

[54] PARTICLE ANALYZING APPARATUS USING A COHERENCE LOWERING DEVICE

[75] Inventor: Hideo Kusuzawa, Kobe, Japan

[73] Assignee: TOA Medical Electronics Co., Ltd., Hyogo-ken, Japan

[21] Appl. No.: 305,657

[22] Filed: Sep. 14, 1994

[30] Foreign Application Priority Data

Sep. 16, 1993 [JP] Japan .................................. 5-230235

[51] Int. Cl.⁶ .............................. G01N 15/14; G06K 9/20
[52] U.S. Cl. ................................. 356/23; 356/72; 356/73
[58] Field of Search ................................. 356/23, 72, 73

[56] References Cited

U.S. PATENT DOCUMENTS

| | | | |
|---|---|---|---|
| 4,361,400 | 11/1982 | Gray et al. | 356/23 |
| 4,659,937 | 4/1987 | Cielo et al. | 250/560 |
| 4,712,912 | 12/1987 | Messerschmidt | 356/73 X |
| 4,786,165 | 11/1988 | Yamamoto et al. | 356/23 |
| 5,159,398 | 10/1992 | Maekawa et al. | 356/23 X |
| 5,272,354 | 12/1993 | Kosaka | 356/574 |

FOREIGN PATENT DOCUMENTS

0436343 A 7/1991 European Pat. Off. .
0543514 A 5/1993 European Pat. Off. .
2202626 9/1988 United Kingdom .

OTHER PUBLICATIONS

Chien et al, "Scale-Factor-Stabilized Fiber-Optic Gyroscope Based On A Spectrum-Broadened Laser-Diode Source", Optics Letters/ vol. 16 No. 6, Mar. 15, 1991, pp. 426-428.

Primary Examiner—Vincent P. McGraw

[57] ABSTRACT

A particle analyzing apparatus includes a flow device having a light-transmissive flow cell for allowing subject particles in a sample liquid to flow in a separated state, a laser beam illuminator for illuminating a subject particle flowing in the flow cell with a laser beam and a coherence lowering device for lowering coherence of the laser beam. The particle analyzing apparatus further includes an image capturing device receiving light from the subject particle, for capturing an image of the subject particle and an image processor for processing and analyzing the captured image of the subject particle. By use of the coherence lowering device, both temporal and spatial coherence of the laser beam is lowered. Thus, image quality is improved and a high quality particle image can be obtained which is bright and high in S/N ratio.

12 Claims, 13 Drawing Sheets

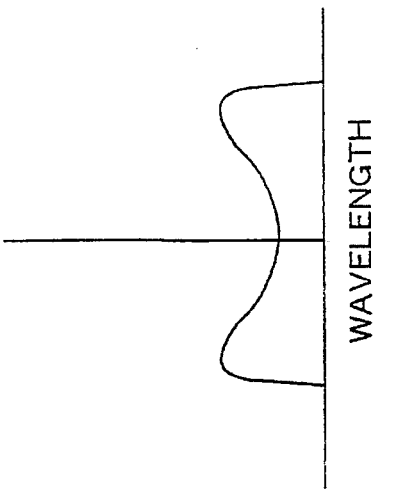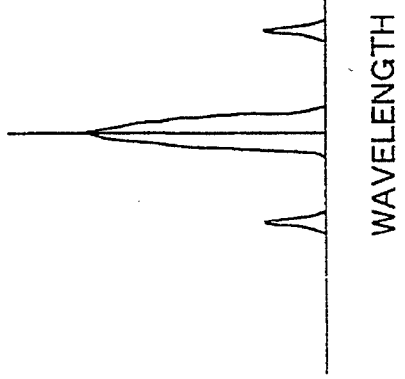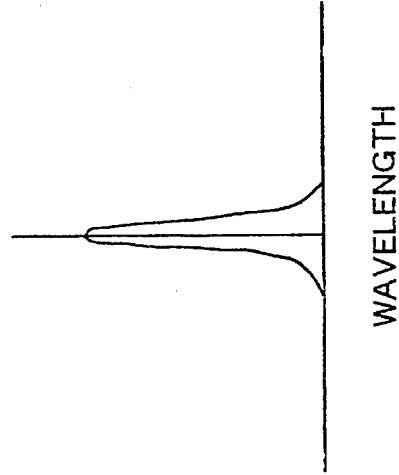

INTENSITY DISTRIBUTION OF INCIDENT LIGHT TO FIBER COLLIMATOR ($l_1$–$l_2$ IS DIAMETER OF INCIDENT LASER BEAM)

INTENSITY DISTRIBUTION OF EXIT LIGHT FROM OPTICAL FIBER ($l_3$–$l_4$ IS EQUIVALENT TO DIAMETER OF INCIDENT LASER BEAM)

INTENSITY DISTRIBUTION OF EXIT LIGHT FROM FINAL OPTICAL LENS ($l_5$–$l_6$ IS EQUIVALENT TO DIAMETER OF WAVEFRONT CONVERTING ELEMENT)

WITH OPTICAL FIBER

WITHOUT OPTICAL FIBER

PARTICLE ANALYZING APPARATUS USING A COHERENCE LOWERING DEVICE

BACKGROUND OF THE INVENTION

1. Field of the Invention

The present invention relates to a particle analyzing apparatus for imaging a particle suspended in a liquid. More specifically, the invention relates to a particle analyzing apparatus for analyzing a particle by introducing a sample liquid obtained by diluting blood, urine, or the like into a flow cell and imaging an individual particle such as a blood cell or a cell in urine.

2. Description of the Related Art

Among the conventional particle analyzing apparatuses of the above kind are an apparatus called a flow cytometer in which particles such as blood cells or other cells are introduced into a flow cell in an arranged manner and an individual particle is measured, and various particle analyzing apparatuses which image a particle such as a blood cell or some other cell and analyze the particle thus imaged.

An example of the flow cytometer is an imaging flow cytometer disclosed in Japanese Unexamined Patent Publication No. Hei. 5-142137 (U.S. Pat. No. 5,272,354) in which a still particle image is obtained by opening a shutter of an image intensifier having a high-speed gating function with continuous light illumination.

An example of the particle analyzing apparatus is a method and apparatus for analyzing cells in a liquid in which a particle detecting optical system is provided in addition to an imaging system, and a pulsed laser is caused to emit light with a predetermined delay after detection of a particle to obtain a still image of the particle as described in Japanese Unexamined Patent Publication No. Sho. 63-94156 (U.S. Pat. No. 4,786,165).

However, the above types of conventional particle analyzing apparatuses have a problem that where a flash lamp is used as a light source in imaging a particle such as a blood cell or some other cell in a flow cell, a clear image cannot be obtained when a sample liquid flows fast.

The light emitting period of a flash lamp is in the order of microseconds, i.e., it is relatively long. Therefore, when the light source having such a long light emitting period is used, a particle moves more than 5 μm if the flow speed of a sample liquid is assumed to be 5 m/sec. Thus, a clear image cannot be obtained due to blurring.

That is, with flash lamp type light sources, it is difficult to attain a short light emitting period in the order of nanoseconds, which is required to prevent blurring from occurring in an image of a fast flowing particle. To obtain a clear image, it is necessary to use, for example, pulsed light sources such as a pulsed laser.

However, when a laser such as a pulsed laser is used, the spatial and temporal coherence of the laser may cause an interference fringe or diffraction, which also makes it difficult to obtain a clear image.

Examples of lasers include a pulsed laser and a CW (continuous wave) laser. A particle imaging system in which a CW laser, rather than a pulsed laser, is combined with a high-speed shutter (gate) also suffers from the problem of an interference fringe etc., and cannot produce a clear image.

As described above, pulsed lasers can realize a light emitting period on the nanosecond order or shorter. Further, lasers can improve the energy density per unit area to enable sufficient energy for imaging to be generated during a short light emitting period or a short gating period. However, in lasers, the spatial and temporal coherence causes an interference fringe, Fresnel diffraction or Fraunhofer diffraction, which deteriorates image quality.

When a sample liquid flows fast in a particle analyzing apparatus, it is necessary to use a light source such as a pulsed laser or a CW laser which can emit high-energy-density light to take a clear particle image. The spatial and temporal coherence is needed to obtain such a high energy density, which however deteriorates image quality.

A theoretical explanation as to why the spatial and temporal coherence causes various types of diffraction and an interference fringe will be made below starting with an analysis of problems we are facing now.

First, a description will be made of how an optical flow cell itself becomes a FP (Fabry-Pérot) interferometer to cause an interference fringe.

Usually, the interference distance of a laser is defined by measuring a distance between two reflecting bodies. (An actual interference fringe is not considered to be caused by reflection by only two particular surfaces of an optical flow cell, but is instead caused by multiple reflection involving four surfaces in total.)

In theory, the interference distance of a laser is determined by the oscillation spectrum width. If the oscillation spectrum width is 30 GHz (corresponding to catalogue data of 1 cm$^{-1}$ of an LD-pumped YAG laser), the difference between mean lifetimes of laser oscillation levels is roughly estimated from the above width such that $$1/(3.0 \times 10^{10}) = 3.3 \times 10^{-11} \text{ sec.}$$

Further, the laser interference distance is calculated as $$(3.0 \times 10^8 \text{ m/sec.}) \times (3.3 \times 10^{-11} \text{ sec.}) = 1.0 \times 10^{-2} \text{ m}$$

Where a flow cell has a shape of 4 mm×4 mm, an interference naturally occurs. In the case of an Ar laser, the laser interference distance is in the order of several kilometers. The narrow oscillation spectrum width is a measure of evaluating the temporal coherence of a laser. An interference fringe can be avoided by increasing the oscillation spectrum width.

Next, an explanation will be made of how Fresnel diffraction and Fraunhofer diffraction occur.

To cause laser oscillation, it is necessary that wavefront phases of respective excited atoms be identical (spatial coherence). The Fresnel diffraction is caused by a plane wave being diffracted by an end face of a cell or the like.

In the Fraunhofer diffraction, a ring-like fringe appears in a converged spot because of varying distances from respective points on the above-mentioned plane wave in the case where the plane wave is not one originating from a point light source but one further converged optically. Therefore, to improve the image quality by weakening the Fraunhofer diffraction, it is necessary to use an optical system which causes random spatial propagation.

According to the current quantum electronics theory and technique, the spatial coherence and the temporal coherence is interrelated and, therefore, it is impossible in a single laser light source to improve or deteriorate one of those.

The present invention has been made in view of the above circumstances, and has an object of providing, with the use of a laser light source for imaging, a particle analyzing apparatus which can obtain a high-quality particle image without being affected by any interference fringe or diffraction by illuminating a particle with a coherence-lowered laser beam.

SUMMARY OF THE INVENTION

The present invention has been made in view of the above circumstances, and has an object of providing, with the use of a laser light source for imaging, a particle analyzing apparatus which can obtain a high-quality particle image without being affected by any interference fringe or diffraction by illuminating a particle with a coherence-lowered laser beam.

The present invention provides a particle analyzing apparatus comprising: flow means having a light-transmissive flow cell for allowing subject particles in a sample liquid to flow in a separated state; laser beam illuminating means for illuminating a subject particle flowing in the flow cell with a laser beam; coherence lowering means for lowering coherence of the laser beam; image capturing means receiving light from the subject particle, for capturing an image of the subject particle; and image processing means for processing and analyzing the captured image of the subject particle.

According to the present invention, the subject particles flowing in the flow cell are illuminated with a laser beam emitted from the laser beam illuminating means, in which the coherence of the laser beam is lowered by the coherence lowering means. An image of a subject particle is captured by the image capturing means, and the captured image of the subject particle is subjected to image processing.

By virtue of the coherence lowering means that lowers the coherence of the laser beam, a high-quality particle image can be obtained which is bright and high in S/N ratio and which is not affected by diffraction nor interference.

Where the apparatus includes a particle detecting means having a judging means, a judgment is made as to whether or not to take an image of a subject particle after it has been detected. Therefore, an abnormal or indefinite particle or an important particle can be imaged selectively to determine, in an image, what kind of particle it is.

These and other objects of the present application will become more readily apparent from the detailed description given hereinafter. However, it should be understood that the preferred embodiments of the invention are given by way of illustration only, since various changes and modifications within the spirit and scope of the invention will become apparent to those skilled in the art from this detailed description.

BRIEF DESCRIPTION OF THE DRAWINGS

The present invention will be detailed in conjunction with the accompanying drawings, but the invention is not limited thereto.

FIG. 3(a); FIG. 3(b) & FIG. (c) illustrate light spectrum variations caused by an optical phase modulating element according to the present invention.

DETAILED DESCRIPTION OF THE PREFERRED EMBODIMENTS

Figure 1:
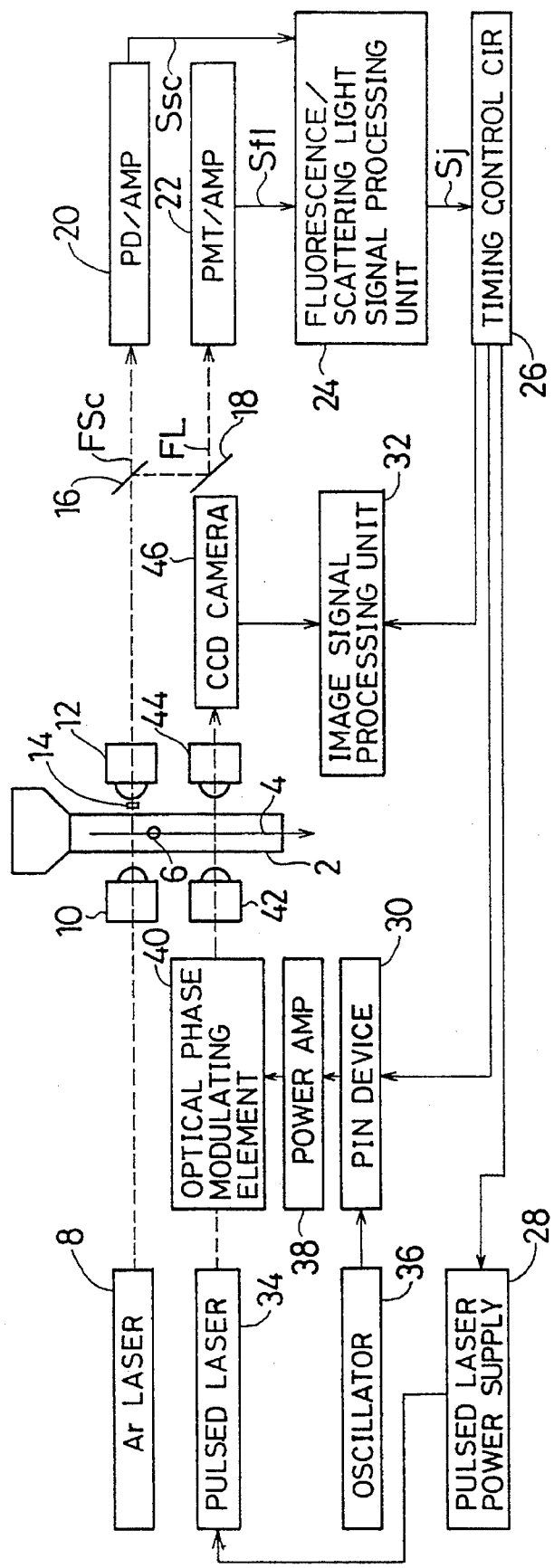
FIG. 1 is a block diagram showing a first embodiment of the present invention.

As the flow device of the invention, various devices can be used which has a light-transmissive flow cell, and can introduce a sample liquid including subject particles into the flow cell and allow the subject particles to flow in a separated state.

A sample liquid including any kind of particles may be introduced into the, flow cell. Primarily, sample liquids obtained by diluting blood, urine, powders, or the like at an arbitrary rate are used. For certain purposes, seawater, lake water, river water, etc. can be used as samples.

A flow cell having a square flow path or a flat flow cell, which are known, are used as the light-transmissive flow cell.

It suffices that the flow cell has such light transmissivity as allows a subject particle flowing in the flow cell to be imaged from outside the flow cell. The flow cell may be made of glass or plastics, or a synthetic resin having the same level of transmittance as those materials.

The laser beam illuminating device may be a laser such as an Ar laser, an LD-pumped YAG plus KTP laser, or an LD (laser diode), which can illuminate, always or at an arbitrary timing, an object with a CW or pulsed laser beam.

The light illumination period of the laser beam illuminating device may be set with respect to the flow speed of a subject particle in the following manner. Where the flow speed of a subject particle and the light illumination period are written as v [m/s] and t [µs], respectively, a blur U in an image of the subject particle is expressed as U=vt. Therefore, if the blur U is smaller than the imaging resolution of the imaging device, a good still image of the subject particle can be obtained. For example, to make the blur U in a subject particle image smaller than 0.3 [µm], the light illumination period t should be set such that t≦60 [ns] when v=5 [m/s].

Various devices capable of lowering the coherence of a laser beam free from non-uniformity in the light intensity can be used as the coherence lowering device.

Any device can be used as the capturing means as long as it can receive light from a subject particle and capture an image thereof. For example, a CCD camera and a video camera on the market can be used.

The image processing device may be an image processing apparatus which can convert image data of a picked-up image of a subject particle to digital data, perform various kinds of image processing on the digital data, and again convert the processed digital image data to output analog data.

In the particle analyzing apparatus according to the invention, the laser beam emitted from the laser illuminating device may be a pulsed laser beam.

The particle analyzing apparatus of the invention may further comprise a particle detecting device for detecting a particle, and a control device for controlling the laser beam illuminating device to cause it to emit the pulsed laser beam after the particle has been detected.

Various types of detecting devices may be used as the above particle detecting device as long as they can detect a particle.

For example, the particle detecting device may consist of a light emitting device for illuminating a sample liquid flow with light, and a photodetecting device for receiving light from the sample liquid. The light emitting device may be a light source such as a lamp or an Ar laser which can always illuminate the object with light. There can be used as the photodetecting device various types of photosensors which can receive forward scattering light or fluorescence from a particle and convert such light to an electrical signal.

The control device may be any device which can control the laser beam illuminating device to cause it to emit a pulsed laser beam after a particle has been detected. The control device may be a control circuit that incorporates a control procedure in the form of hardware or software and is constituted, for instance, of a gate circuit or a microcomputer including a CPU, ROM, RAM and I/O port.

In the particle analyzing apparatus according to the invention, the laser beam emitted from the laser beam illuminating device may be a CW laser beam. Further, a gating device for limiting the light entering the imaging device is disposed between the flow device and the imaging device. There can be used as the gating various types of optical elements having a gating function such as an image intensifier and a liquid crystal switch.

The particle analyzing apparatus according to the invention may further comprise a particle detecting device for detecting a particle in an illuminated region of the sample liquid being illuminated by the laser beam illuminating device, and a control device for causing the imaging device to take an image of the subject particle while controlling the gating device after the particle has been detected.

The control device may be any device which can cause the imaging device to take an image of the subject particle while controlling the gating device after the particle has been detected. Like the above-mentioned control device, the control means concerned may be a control circuit that incorporates a control procedure in the form of hardware or software and is constituted, for instance, of a gate circuit or a microcomputer including a CPU, ROM, RAM and I/O port.

In the particle analyzing apparatus according to the invention, it is preferred that the particle detecting device includes a judging device for analyzing the detected particle to judge whether to capture an image of the detected particle based on an result of the analysis.

In the particle analyzing apparatus according to the invention, the coherence lowering device may comprise an optical phase modulating element for increasing a spectrum width of a light beam.

In this case, the optical phase modulating element may be Constituted, for instance, by incorporating an electro-optic crystal (also called a nonlinear crystal) such as $LiNbO_3$, $LiTaO_3$ or $TeO_2$ in a microwave resonator. For example, "Bulk Electro-Optic Modulator 4841" of NEW FOCUS, Inc. can also be used as the optical phase modulating element.

The above optical phase modulating element is used such that while a laser beam is passed through the electro-optic crystal, a microwave is input to the microwave resonator from an external drive device. Thus, the spectrum width of the laser beam transmitted from the electro-optic crystal is increased and the temporal coherence is lowered.

It is possible to get the above electro-optic crystal and manufacture an optical phase modulating element in person.

With the above configuration, by virtue of the resonance in the microwave resonator, a strong electric field can be produced with a small input power. By orienting the electro-optic crystal in the direction which enables full use of the above electric field and the electro-optical effect of the crystal, light frequency phase modulation can be performed efficiently. The light frequency means the wave of a light beam. For example, since the speed of light is $3\times10^8$ m/sec., a light beam having a wavelength of 0.532 μm has a frequency of 563 THz.

In the particle analyzing apparatus according to the invention, the coherence lowering device may comprise a single-mode optical fiber for providing random space propagation of the light beam.

Further, the coherence lowering device may comprise the single-mode optical fiber for providing random space propagation of the light beam and a wavefront converting element.

In this case, it is preferred that a single-mode optical fiber be used which propagates a laser beam in a single mode with respect to the wavelength of the used laser beam. With the use of the single-mode optical fiber, not only a variation in the two-dimensional light intensity distribution of the input pulse light can be suppressed but also the light energy density is increased within the propagation core, which cause the self-converging effect and the self-phase-modulation effect. Therefore, it is possible to lower both of the spatial coherence and the temporal coherence.

There may used as the wavefront converting element a stainless seamless pipe whose internal surface is optically polished, a glass cylinder in which both end faces and the cylindrical circumferential surface are optically polished and the cylindrical circumferential surface is subjected to aluminum evaporation to enable light reflection, or a multi-mode optical fiber of a large diameter.

Figure 10A:
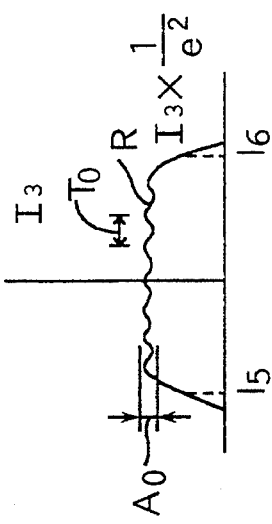
FIG. 10(a)
Figure 10B:
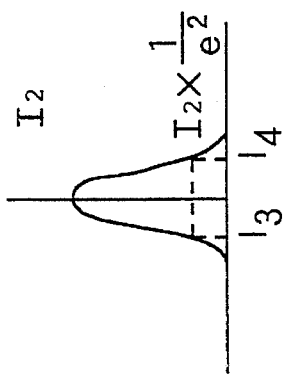
FIG. 10(b) & FIG. 10(c) show light intensity distributions obtained when the optical fiber and the wavefront converting element according to the present invention are used.
Figure 10C:
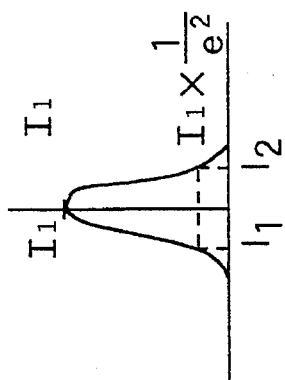

The length of the wavefront converting device should be longer than 10 mm, and its outside diameter should be selected so that after a laser beam is condensed by a condenser lens 42, a ripple R in a light intensity distribution shown in FIG. 10(c) becomes less than the resolution of an optical system. That is, an amplitude $A_0$ of the ripple R in the light intensity distribution of FIG. 10(c) should be smaller than the light intensity resolution of an imaging system, or a period $T_0$ of the ripple R should be smaller than the two-dimensional resolution. In short, influences of the ripple R in a picked-up image should be avoided.

Since the period $T_0$ of the ripple R changes depending on the properties of the used light source of the pulsed laser beam, a Kälher illumination system is preferably adopted as an illumination optical system including a light collecting system in the laser illumination system to obtain a favorable image.

When a multi-mode optical fiber is used as the wavefront converting element, the two-dimensional light intensity distribution can further be stabilized by fixing the multi-mode optical fiber so that it assumes a linear shape.

When the optical fiber and the wavefront converting element are combined, the laser beam is input to the optical fiber, and an output light beam of the optical fiber is directly input to the wavefront converting element.

Further, in the particle analyzing apparatus according to the invention, the coherence lowering device may comprise the optical phase modulating element for increasing the spectrum width of the light beam, the single-mode optical fiber for providing random space propagation of the light beam and the wavefront converting element.

In this case, it is preferred that the coherence lowering device is consituted in such a manner that the optical phase converting element, the single-mode optical fiber and the the wavefront converting element are arranged in this order along the traveling direction of the light beam.

In the following, the present invention will be described in detail by way of first to fourth embodiments that are illustrated by the drawings. However, it is noted that the invention is in no way limited to those embodiments. In the following description, the first, third and fourth embodiments are directed to the case where a particle image is taken by use of a pulsed laser, and the second embodiment is directed to the case where a particle image is taken by use of a CW(continuous wave) laser.

Embodiment 1

FIG. 1 is a block diagram showing a configuration of a particle analyzing apparatus according to the first embodiment of the invention.

In this particle analyzing apparatus, a stable sample flow is formed by introducing a sample liquid obtained by diluting blood, urine, or the like into a transparent flow cell. While the sample flow is illuminated with a laser beam, an image of a particle (also called a "subject particle" when it is examined) such as a blood cell included in blood or a cell included in urine is taken by a CCD camera. The particle image thus taken is subjected to image processing.

In FIG. 1, reference numeral 2 denotes a light-transmissive flow cell made of glass or plastics. When a sample liquid is introduced into the flow cell 2, a sheath liquid is also supplied so as to surround the sample liquid. That is, a laminar flow of the sample liquid and the sheath liquid flows in the flow cell 2.

Reference numeral 4 denotes a sample flow that is flowing in the flow cell 2. Particles 6 such as blood cells or some other cells included in the sample flow 4 are flowing in the flow cell 2 in a separated state.

Reference numeral 8 denotes an Ar laser beam emitting device for illuminating the sample flow 4 flowing in the flow cell 2 with an Ar laser beam as a CW laser beam; 10, a condenser lens; 12, an objective lens; 14, a beam stopper disposed between the flow cell 2 and the objective lens 12.

Reference numerals 16 and 18 represent a wavelength selecting filter and a reflecting mirror 18, respectively. A PD/amplifier 20 of a detecting system for forward scattering light processing receives forward scattering light (FSc) as selected by the wavelength selecting filter 16, and outputs a detection signal Ssc. A PMT/amplifier 22 of a fluorescence detecting system receives fluorescence (FL) that has not been selected by the wavelength selecting filter 16, and outputs a detection signal Sfl.

A fluorescence/scattering light signal processing unit 24 receives the detection signals Ssc and Sfl, and processes those signals to obtain information on the particle 6. If the unit 24 judges that an image of the particle 6 is necessary, it outputs a judgment signal Sj.

A timing control circuit 26 receives the judgment signal Sj from the fluorescence/scattering light signal processing unit 24, and supplies a power supply signal to a pulsed laser power supply 28, a gate opening signal to a PIN device 30, and an image taking-in start signal to an image signal processing unit 32.

Powered by the pulsed laser power supply 28, an LD-pumped YAG plus KTP pulsed laser beam illuminating device 34 illuminates the flow cell 2 with a pulsed laser beam.

Reference numeral 36 denotes an oscillator for always generating a microwave. When receiving the gate opening signal from the timing control circuit 26, the PIN device 30 pulse-modulates the microwave supplied from the oscillator 36. Reference numeral 38 represents a power amplifier.

Receiving the pulse-modulated microwave from the power amplifier 38, an optical phase modulating element 40 increases the spectrum width of the pulsed laser beam to thereby mainly lower its temporal coherence mainly.

Reference numerals 42 and 44 denote a condenser lens and an objective lens, respectively. A CCD camera 46 receives a laser beam that is output from the particle 6 when it is illuminated with the low-coherence light beam, and captures an image of the particle 6.

The image signal processing unit 32 processes the particle image taken by the CCD camera 42.

Figure 2:
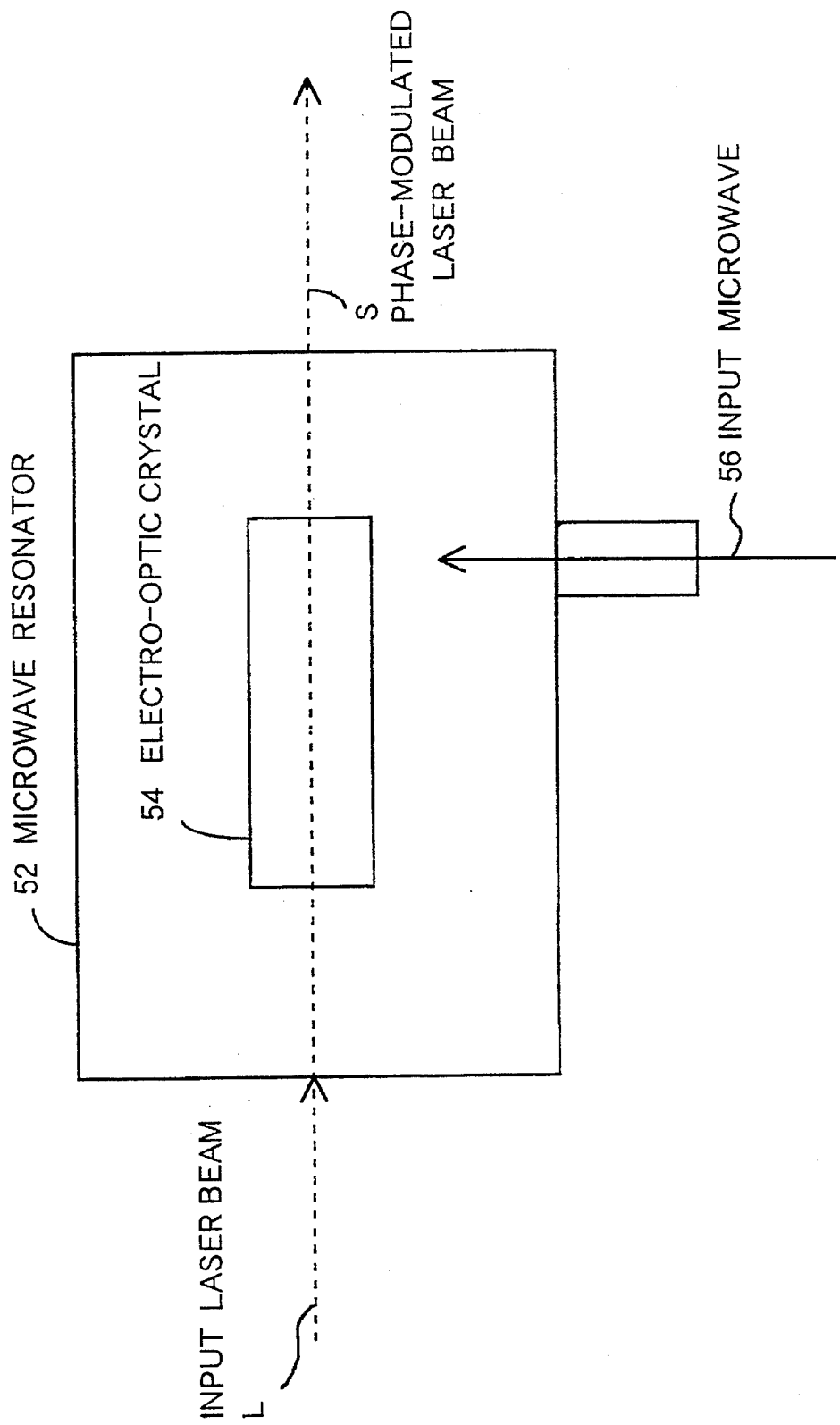
FIG. 2 illustrates a conceptual configuration of an optical phase modulating element according to the present invention.

FIG. 2 shows a conceptual configuration of the optical phase modulating element 40. As shown in FIG. 2, the optical phase modulating element 40 is constituted such that $LiNbO_3$ or $LiTaO_3$ as an electro-optic crystal (also called a nonlinear crystal) 54 whose refractive index is varied by an electric field through variations of crystal constants is incorporated in a microwave resonator 52. A microwave 56 can be externally input to the device 40.

The microwave resonator 52 receives not only a laser beam L but also the microwave 56 from the oscillator 36 via the PIN device 30 and the power amplifier 38. The laser beam L is phase-modulated in the microwave resonator 52, and a phase-modulated laser beam S is output therefrom. In this manner, the spectrum width of the laser beam passing through the electro-optic crystal 54 is increased to lower its temporal coherence.

With the above configuration, by virtue of the resonance in the microwave resonator 52, a strong electric field can be produced with a small input power. The laser beam can be phase-modulated efficiently by orienting the electro-optic crystal 54 in the direction that enables effective use of the electric field and the electro-optical effect of the electro-optic crystal 54.

FIGS. 3(a), 3(b) and 3(c) show light spectrum variations caused by the optical phase modulating element 40. FIG. 3(a) shows an oscillation spectrum of the light beam input to the optical phase modulating element 40. FIGS. 3(b) and 3(c) show oscillation spectra of light beams modulated by the optical phase modulating element 40, in which FIG. 3(b) corresponds to a low-modulation case and FIG. 3(c) corresponds to a high-modulation case. As shown in FIG. 3, in the case of low modulation, there is obtained a spectrum shape that is discrete as a whole (equivalent to spectra of frequency modulation and pulse modulation). In the case of high modulation, there is obtained a spectrum shape covering a wide, continuous range. (The use of a high resolution optical spectrometer in the spectrometry allows the spectra in FIG. 3(c) to be observed as a collective body of dispersed oscillation spectra.)

Therefore, in various flow cytometry systems (even other than particle analyzing apparatuses like this embodiment), a clear monochromatic image can be taken by disposing the optical phase modulating element 40 between a light source and an end face of an optical reflecting body (flow cell 2 in this embodiment), and increasing the spectrum width of a laser beam to such an extent that no interference fringe is caused.

The coherence can be lowered even when the single-mode optical fiber is used in place of the optical phase modulating element 40

In this embodiment, the imaging system from the pulsed laser beam emitting device 34 to the CCD camera 46 is disposed perpendicularly to the optical system for detecting the forward scattering light and the fluorescence coming from the particle 6 in the flow cell 2 when illuminated by the Ar laser beam emitting device 8.

The operation of the above particle analyzing apparatus will be hereinafter described.

When a laser beam is continuously applied from the Ar laser beam emitting device 8 to the particle 6 in the flow cell 6, forward scattering light and fluorescence coming from the particle 6 are detected by the PD/amplifier 20 and the PMT/amplifier 22, respectively.

The detection signals Ssc and Sfl output from the PD/amplifier 20 and the PMT/amplifier 22 are processed by the fluorescence/scattering light signal processing unit 24, and cell information of the particle 6 is obtained. If it is judged that an image of the particle 6 is necessary, the fluorescence/scattering light signal processing unit 24 sends the judgment signal Sj to the timing control circuit 26.

In response to a judgment signal Sj, the timing control circuit 26 sends a trigger signal to the pulsed laser power supply 28. In response thereto, the pulsed laser beam illuminating device 34 emits a pulsed laser beam, which is applied to the particle 6 in the flow cell 2.

In the above operation, there is needed a time difference that includes a processing and judging time of the fluorescence/scattering light signal processing unit 24 and a delay of the respective electronic systems from the detecting system to the pulsed laser beam illuminating device 34. Therefore, the Ar laser beam illuminating position and the pulsed laser beam illuminating position has such a distance as allows at least the above time difference.

In synchronism with the trigger signal to the pulsed laser power supply 28, a gate-opening trigger signal is sent from the timing control circuit 26 to the PIN device 30, and a microwave that is always generated from the oscillator 36 is pulse-modulated and supplied to the optical phase modulating element 40. As a result, the spectrum width of a pulsed laser beam as output from the pulsed laser beam illuminating device 34 is increased, and then the resulting pulsed laser beam is applied to the particle 6.

As described above, by using the optical phase modulating element 40, it becomes possible to image the particle 6 in the flow cell 2 without being affected by an interference fringe nor diffraction light. Further, since the particle 6 is analyzed based on the forward scattering light and the fluorescence, it is possible to selectively image only a singular cell including an abnormal cell, and present its image.

The imaging ability (the number of images taken per unit period) is limited by the ability on the image signal processing unit 32 side when the image processing ability of the image signal processing unit 32 is low, and by the pulsed laser beam emittable time (the period of light emission) of the pulsed laser beam illuminating device 34 when the image processing ability of the image signal processing unit 32 is high.

As for the CCD camera 46, a product having an imaging ability of 40,500 images/sec is currently on the market. Where this CCD camera is employed in the above apparatus, currently available Q-switch pulsed lasers cannot accommodate such high repetition rate imaging. In such a case, the method of the second embodiment described below is promising.

Embodiment 2

Figure 4:
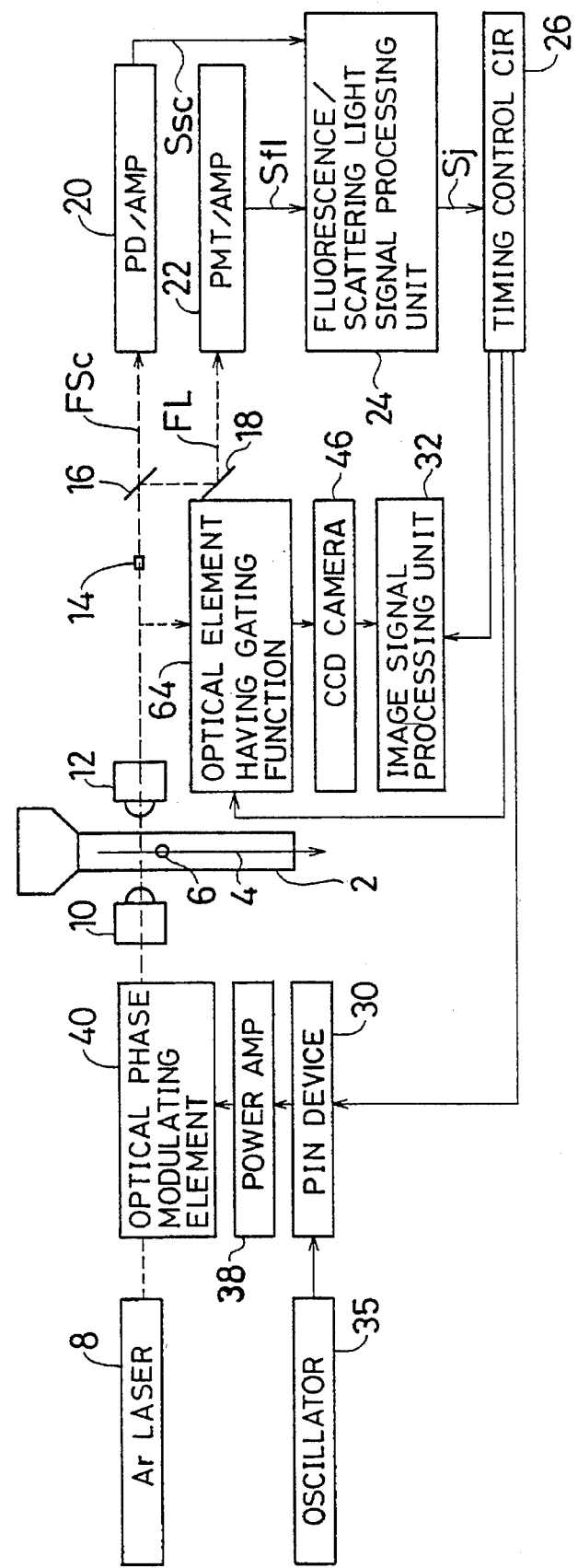
FIG. 4 is a block diagram showing a configuration of a second embodiment of the present invention.

FIG. 4 is a block diagram showing a configuration of a particle analyzing apparatus according to the second embodiment of the invention. The components shown in FIG. 4 that are the same as those in the first embodiment are given the same reference numerals, and descriptions therefor are omitted.

The second embodiment is basically the same as the first embodiment, and is different from it in the following points. That is, while in the first embodiment the Ar laser beam emitting device 8 for the particle detection and the pulsed laser beam illuminating device 34 for the particle imaging are separately provided, in the second embodiment only the CW Ar laser beam emitting device 8 is used which serves for both particle detection and particle imaging.

Further, in the second embodiment, a half mirror 62 is provided which separates a light beam going to the detecting system and a light beam going to the CCD camera 46, and an optical element 64 having a gating function, such as an image intensifier or a liquid crystal switch, is disposed in front of the CCD camera 46.

Therefore, while in the first embodiment the analyzing amount of particles that can be imaged is determined by the period of laser beam emission, in the second embodiment a large number of particles can be imaged in accordance with the gate opening/closing speed of the optical element 64 having a gating function irrespective of the period of laser beam emission, because the imaging operation of the CCD camera 46 is electrically controlled by the optical element 64 having a gating function.

This embodiment operates in the following manner.

When the particle 6 in the flow cell 2 is continuously illuminated with a laser beam emitted from the Ar laser beam emitting device 8, forward scattering light and fluorescence coming from the particle 6 are detected by the PD/amplifier 20 and the PMT/amplifier 22, respectively. Although the laser beam passes through the optical phase modulating element 40, the optical phase modulating element 40 is not in operation because it receives no signal from the power amplifier 38.

The detection signals Ssc and Sfl output from the PD/amplifier 20 and the PMT/amplifier 22 are processed by the fluorescence/scattering light signal processing unit 24, and cell information of the particle 6 is obtained. If it is judged that an image of the particle 6 is necessary, the fluorescence/scattering light signal processing unit 24 sends the judgment signal Sj to the timing control circuit 26.

In response to a judgment signal Sj, the timing control circuit 26 sends a gate-opening trigger signal to the pulsed laser power supply 28. In response, the microwave that is always generated from the oscillator 36 is pulse-modulated, and the modulated microwave is supplied to the optical phase modulating element 40. As a result, the spectrum width of the laser beam emitted from the Ar laser beam emitting device 8 is increased, and the resulting laser beam is applied to the particle 6.

In the above operation, it is required that the particle 6 remain in the imaging field of the CCD camera 46 in a time period that includes a processing and judging time of the fluorescence/scattering light signal processing unit 24 and a delay of the respective electronic systems from the detecting system to the optical element 64 having a gating function.

In synchronism with the trigger signal to the PIN device 30, a gate-opening trigger signal is sent from the timing control circuit 26 to optical element 64 having a gating function during a period necessary for imaging.

The low-coherence light beam applied to the particle 6 is reflected by the half mirror 62, and reaches the optical element having a gating function. At this time, since the gate of the optical element 64 is opened, a particle image is taken by the CCD camera 46.

Since the optical element 64 having a gating function can be on/off-controlled at an extremely high speed, much more images can be taken than in the first embodiment.

As described above, an image of the particle 6 can be taken with the Ar laser(CW laser) beam emitting device 8 functioning as both the light source for the detection of the forward scattering light and fluorescence and the light source for the imaging, i.e., functioning both as the light source for the particle detection and as the light source for the particle imaging.

Embodiment 3

Figure 5:
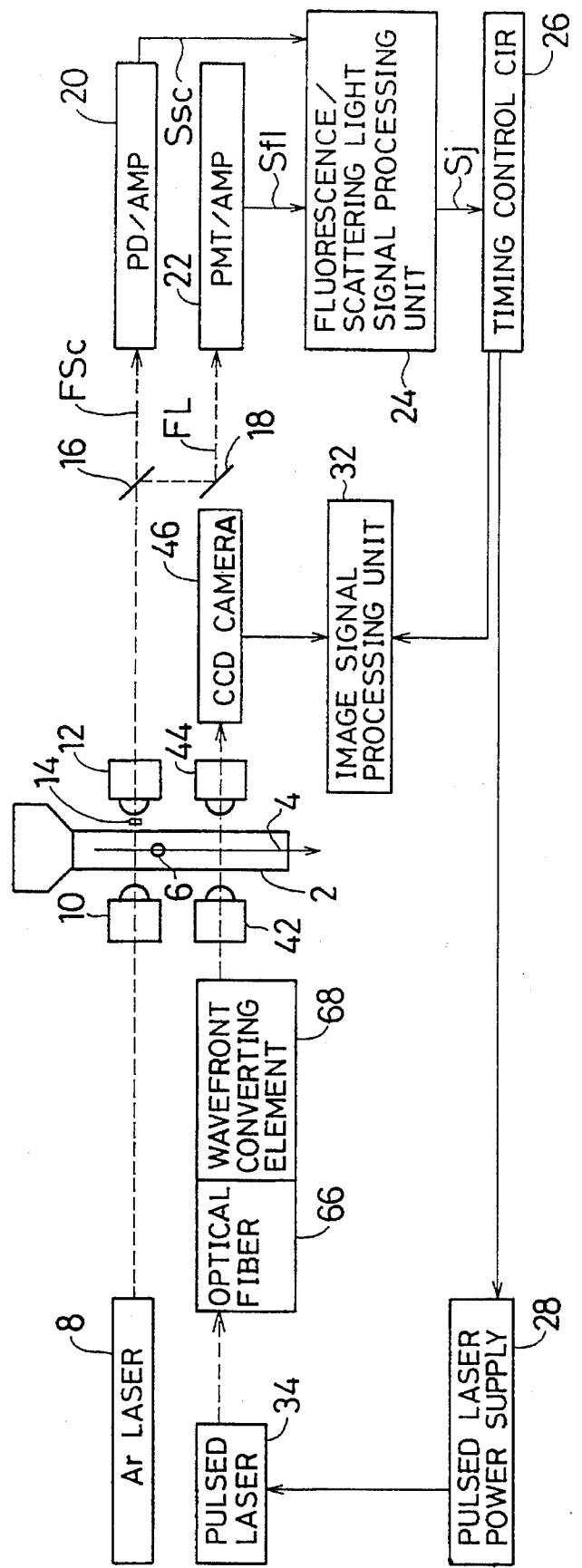
FIG. 5 is a block diagram showing a configuration of a third embodiment of the present invention.

FIG. 5 is a block diagram showing a configuration of a particle analyzing apparatus according to the third embodiment of the invention. The components shown in FIG. 5 that are the same as those in the first embodiment are given the same reference numerals, and descriptions therefor are omitted.

The third embodiment is basically the same as the first embodiment, and is different from it in that an optical fiber 66 and a wavefront converting element 68 are substituted for the optical phase modulating element 40.

A laser beam emitted from the pulsed laser beam illuminating device 34 is input to the optical fiber 66 and the wavefront converting element 68 to effect wavefront conversion of the laser beam. As a result, the space propagation of the laser beam passed through the optical fiber 66 and the wavefront converting element 68 is made random, so that the spatial coherence of the laser beam is mainly lowered.

Figure 6:
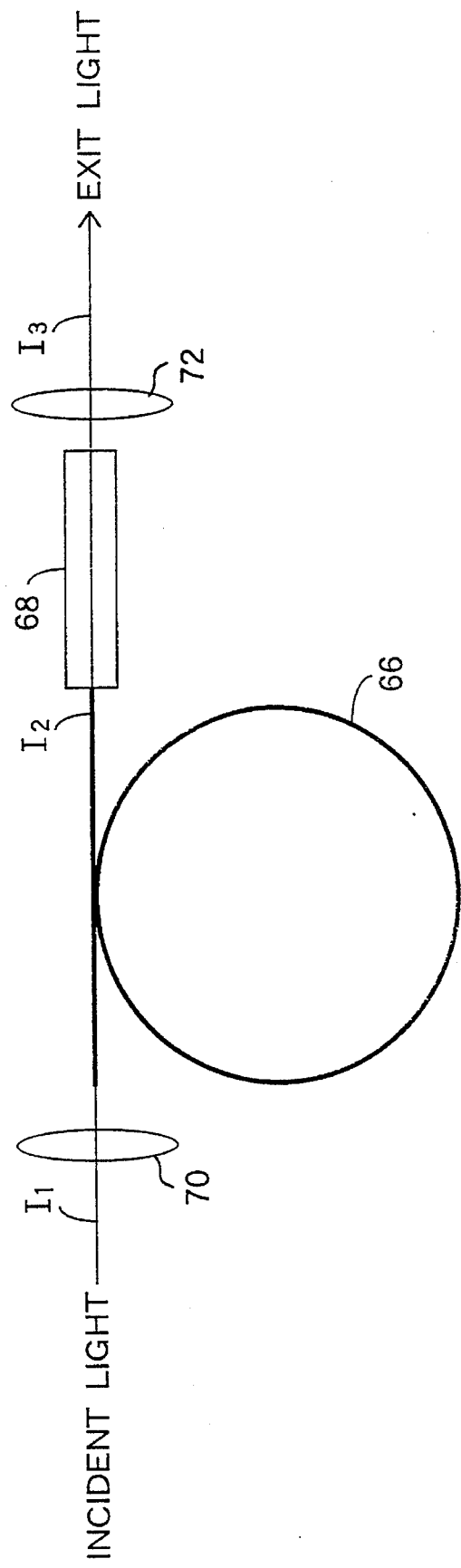
FIG. 6 illustrates a detailed arrangement of an optical fiber and a wavefront converting element according to the present invention.

FIG. 6 shows a detailed arrangement of the optical fiber 66 and the wavefront converting element 68. The optical fiber 66 and the wavefront converting element 68 are arranged continuously. A fiber collimator 70 for condensing an input light beam is disposed in front of the optical fiber 66, and an optical lens 72 for collimating a laser beam is disposed in rear of the wavefront converting element 68.

Figure 7:
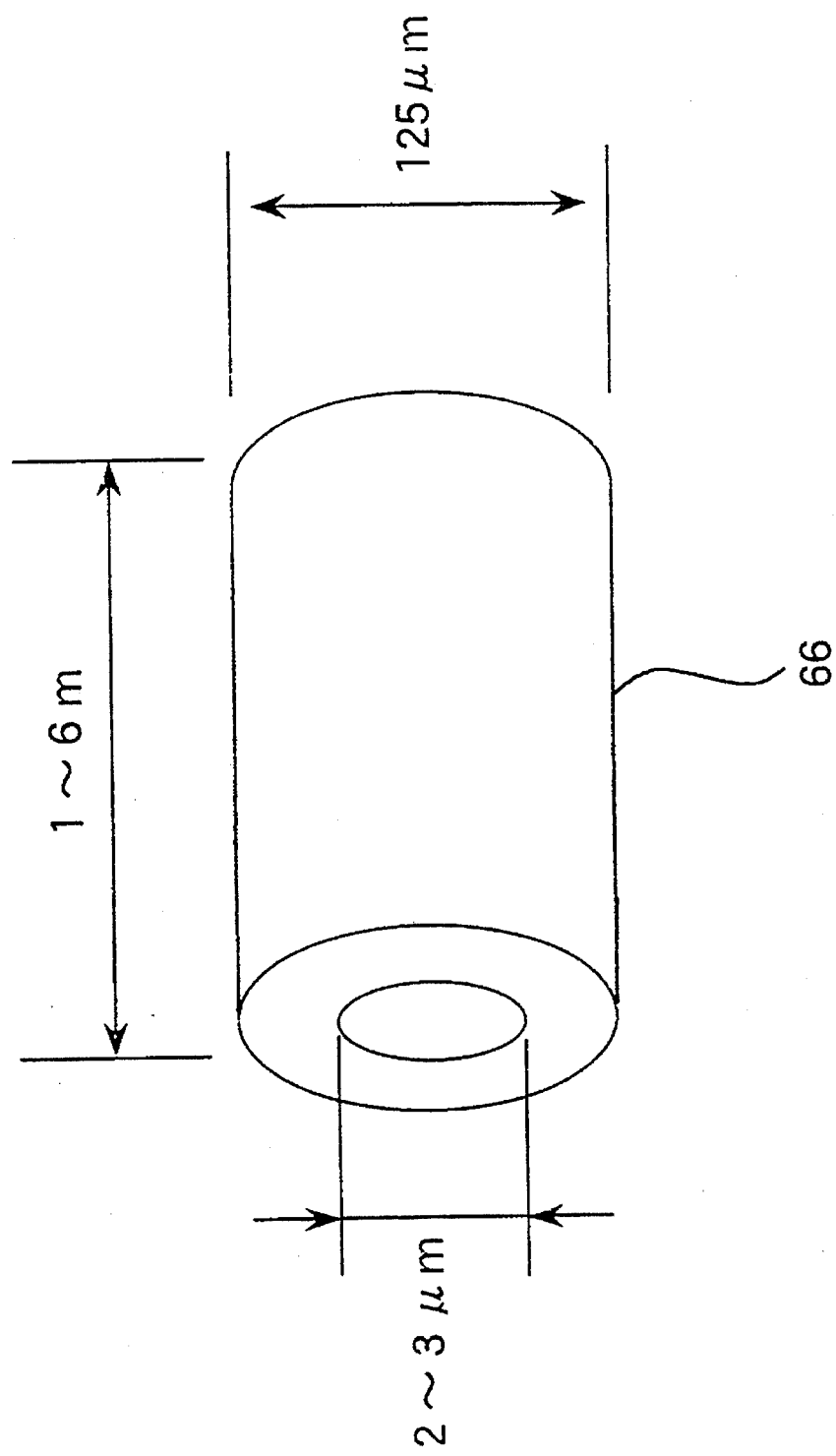
FIG. 7 illustrates a shape of the optical fiber according to the present invention.

As shown in FIG. 7, a single-mode optical fiber having an outside diameter of 125 μm, a core diameter of 2–3 μm, and a length of 1–6 m is used as the optical fiber 66. For example, "PM-048" of Sumitomo Electric Industries, Ltd. can be used.

Figure 8:
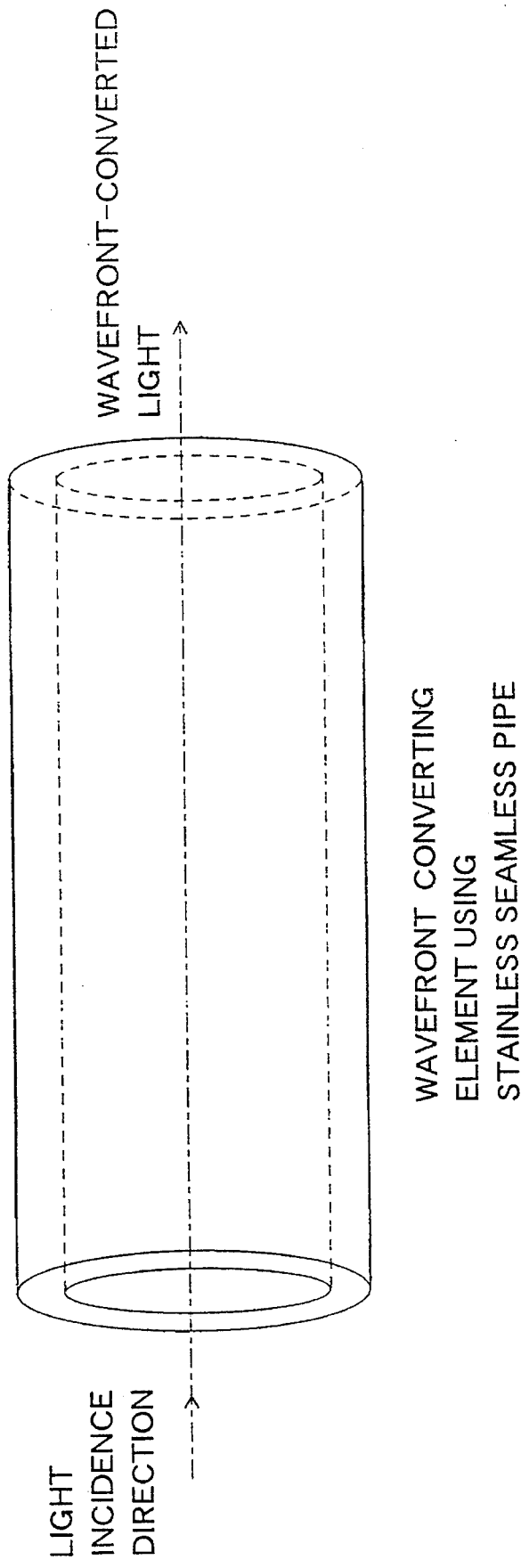
FIG. 8 illustrates a shape of the wavefront converting element according to the present invention.
Figure 9:
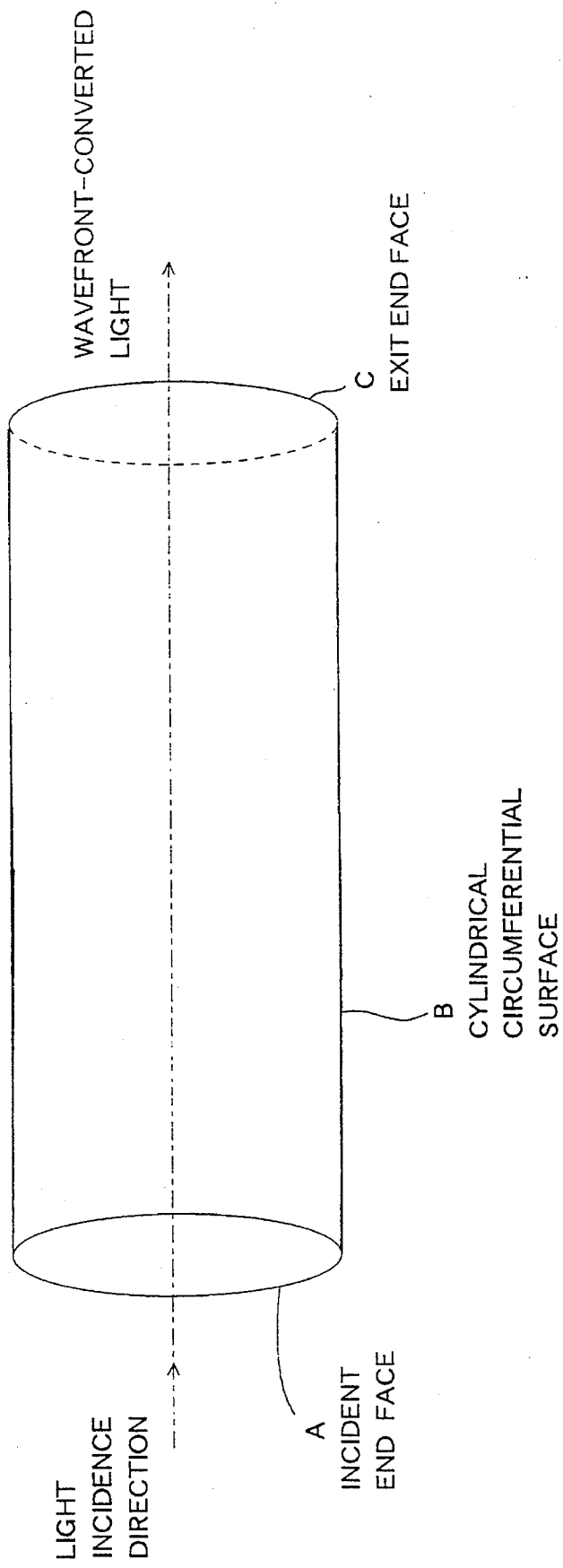
FIG. 9 illustrates another shape of the wavefront converting element according to the present invention.

As shown in FIG. 8, a stainless seamless pipe (inside diameter is 1 mm, for instance) which has a length of more than 10 m and whose inner surface is optically polished can be used as the wavefront converting element 68. A glass cylinder in which an incident end face A, an exit end face C and a cylindrical circumferential surface B are optically polished and the cylindrical circumferential surface has been subjected to aluminum evaporation to enable light reflection (see FIG. 9), and a multi-mode optical fiber of a large diameter (for instance, "SPC-10" of Sumitomo Electric Industries, Ltd.) having a length of 100 mm can also be used as the wavefront converting element 68.

FIGS. 10(*a*), 10(*b*) and 10(*c*) show light intensity distributions obtained when the optical fiber 66 and the wavefront converting element 68 are used, in which FIG. 10(*a*) shows an intensity distribution of an incident light beam $I_1$ to the fiber collimator 70 shown in FIG. 6; FIG. 10(*b*) shows an intensity distribution of an exit light beam $I_2$ from the optical fiber 66 shown in FIG. 6; and FIG. 10(*c*) shows an intensity distribution of an exit light beam $I_3$ from the optical lens 72 shown in FIG. 6 for collimating the laser beam.

As shown in these figures, in FIG. 10(*a*), the intensity distribution of the incident light beam $I_1$ conforms to beam diameters $l_1$–$l_2$ of the incident laser beam. In part FIG. 10(*b*), the intensity distribution of the exit light beam $I_2$ from the optical fiber 66 conforms to core diameters $l_3$–$l_4$ of the optical fiber 66. However, the exit angle is larger than the incidence angle. In FIG. 10(*c*), the intensity distribution of the exit light beam $I_3$ from the optical lens 72 conforms to diameters $l_5$–$l_6$ of the wavefront converting element 68 and the incidence angle with respect to the wavefront converting element 68. The exit angle with respect to the wavefront converting element 68 is larger than the incidence angle with respect to the same.

In the above configuration, the outside diameter of the wavefront converting element 68 should be such that after the laser beam is condensed by the condenser lens 42, a ripple R in the light intensity distribution of FIG. 10(*c*) is smaller than the resolution of the optical system. That is, an amplitude $A_0$ of the ripple R in the light intensity distribution of FIG. 10(*c*) should be smaller than the light intensity resolution of the imaging system, or a period $T_0$ of the ripple R should be smaller than the two-dimensional resolution of the imaging system. In short, it should be avoided that the ripple R influences a picked-up image.

Where a multi-mode optical fiber is used as the wavefront converting element 68, the two-dimensional light intensity distribution can further be stabilized by fixing the multi-mode optical fiber so that it assumes a linear shape.

Embodiment 4

Figure 11:
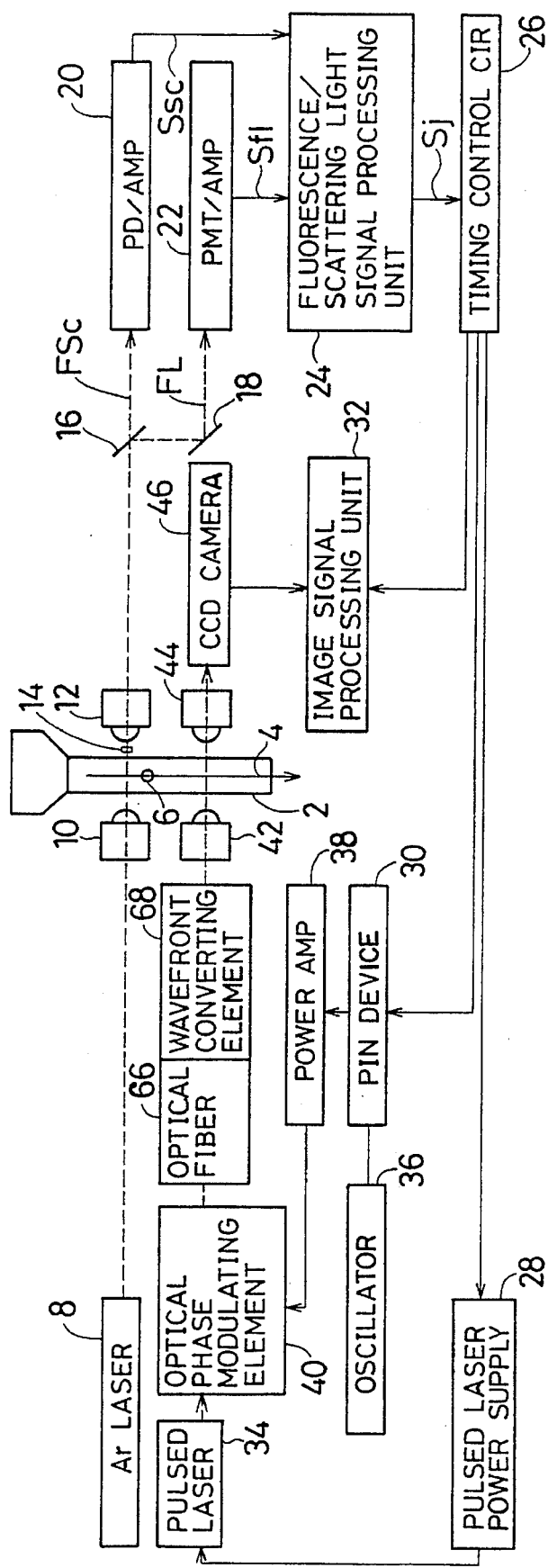
FIG. 11 is a block diagram showing a configuration of a fourth embodiment of the present invention.

FIG. 11 is a block diagram showing a configuration of a particle analyzing apparatus according to the fourth embodiment of the invention. The components shown in FIG. 11 that are the same as those in the first and third embodiments are given the same reference numerals, and descriptions therefor are omitted.

The fourth embodiment is a combination of the configurations of the first and third embodiments, in which the optical phase modulating element 40 of the first embodiment and the optical fiber 66 and the wavefront converting element 68 of the third embodiment are used in combination.

Therefore, a pulsed laser beam is input to the optical phase modulating element 40 to phase-modulate the pulsed laser beam, and then the resulting pulsed laser beam is input to the optical fiber 66 and the wavefront converting element 68 to subject it to the wavefront conversion. In this manner, the temporal coherence of the pulsed laser beam is mainly lowered by the optical phase modulating element 40, and its spatial coherence is mainly lowered by the optical fiber 66 and the wavefront converting element 68.

With the above configuration, the temporal coherence and the spatial coherence of the laser beam can be lowered at the same time. Incidentally, it is possible to use a laser light source which incorporates an optical phase modulating element instead of using the separate laser light source and optical phase modulating element.

From the viewpoint of comparison between the imaging result of the particle analyzing apparatus which uses a coherence lowering device of the present invention and the imaging result of the particle analyzing apparatus which does not use the coherence lowering device of the present invention, usage of only the optical fiber described in Japanese Unexamined Patent Application No. Sho 63-94156, or a multiple-mode optical fiber results in the generation of luminous points (speckle patterns) on the effective illumination surface by the propation mode, thereby deteriorating the image quality.

Figure 12:
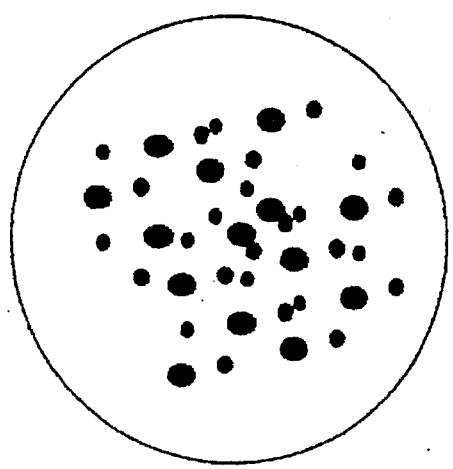
FIG. 12 is an explanatory view showing the light intensity distribution on the illumination surface when only the multiple-mode optical fiber is used.

FIG. 12 is a explanatory view showing the light intensity distribution on the illumination surface when only the multi-mode optical fiber is used. As shown in FIG. 12, when only the multi-mode optical fiber is used, the light intensity distribution becomes non-uniform.

Further, even when frosted glass is used which is described in Japanese Unexamined Patent Application No. Hei 5-142137, speckle patterns are generated on the effective illumination surface. The reason for the phenomenon is described hereinbelow.

When frosted glass is prepared, grinding sands are blown onto the glass with a result that fine lines on the order of the wavelength are generated. The lines produce Fresnel diffraction or the like, which prevents the formation of an illumination surface having a uniform light intensity. It is known that the frosted glass is rotated at a high speed when particles are imaged with a CW laser using the frosted glass. However, such an imaging method cannot be used to image cells flowing at a high speed.

Then, to solve such a problem and to improve the image quality, the present invention uses the optical phase modulating element 40 and the single-mode optical fiber 66.

Figure 13:
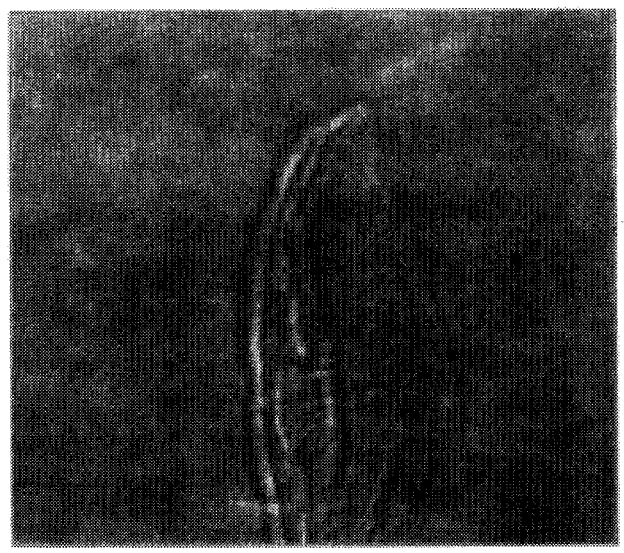
FIG. 13 is a photograph showing the imaging result of the particle analyzing apparatus of the present invention which uses an optical fiber.
Figure 14:
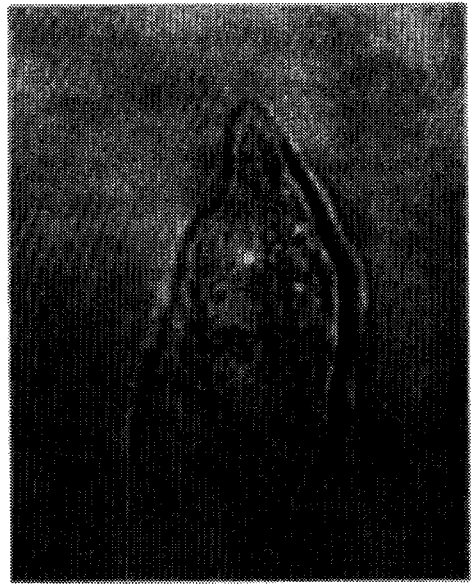
FIG. 14 is a photograph showing the imaging result of the particle analyzing apparatus which does not use the optical fiber.

FIG. 13 and FIG. 14 are photographs showing the comparison between the imaging result of the particle analyzing apparatus of the present invention which uses the optical fiber and the imaging result of the particle analyzing apparatus which does not use the optical fiber.

FIG. 13 shows an example in which epidermal cells are imaged using the optical fiber whereas FIG. 14 shows an example in which epidermal cells are imaged without using the optical fiber. FIG. 13 shows that a high quality image of epidermal cells are obtained free from moire patterns. It is apparent the image quality is improved over the example in which the optical fiber is not used.

According to the present invention, since the apparatus is provided with the coherence lowering device for lowering coherence of a laser beam emitted from the laser beam illuminating device, a high-quality particle image can be obtained which is bright and high in S/N ratio and which is not affected by diffraction nor interference. Further, since particle images can be taken with a lapse of time, the apparatus of the invention is suitable for observation of an agglutination process of particles.

Where the apparatus includes the particle detecting device having the judging device, a judgment is made as to whether or not to take an image of a particle after it is detected. Therefore, a particular particle such as an abnormal or indefinite particle or an important particle can be imaged selectively to determine, on an image, what kind of particle it is. A particle image taken in this manner is highly valuable for support of particle classification results.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A particle analyzing apparatus comprising:

flow means, having a light-transmissive flow cell, for allowing subject particles in a sample liquid to flow in a separated state;

laser beam illuminating means for illuminating at least one of the subject particles flowing in the flow cell with a laser beam;

coherence lowering means for lowering coherence of the laser beam by nonlinear optical effect;

capturing means receiving light from the at least one subject particle, for capturing an image of the at least one subject particle; and image processing means for processing and analyzing the captured image of the at least one subject particle.

2. The particle analyzing apparatus according to claim 1, wherein the coherence lowering means includes an optical phase modulating element having a microwave resonator with an electro-optic crystal incorporated therein and an oscillator for generating a microwave to be received in the microwave resonator, the optical phase modulating element being constructed in such a manner that the laser beam passes through the electro-optic crystal.

3. The particle analyzing apparatus according to claim 1, wherein the coherence lowering means includes a single-mode optical fiber.

4. The particle analyzing apparatus according to claim 1, wherein the coherence lowering means includes a single-mode optical fiber and a wavefront converting element.

5. The particle analyzing apparatus according to claim 1, wherein the coherence lowering means includes an optical phase modulating element, a single-mode optical fiber and a wavefront converting element.

6. The particle analyzing apparatus according to claim 5, wherein the coherence lowering means includes the optical phase modulating element, the single-mode optical fiber and the wavefront converting element arranged in sequential order along a traveling direction of the laser light beam.

7. The particle analyzing apparatus according to claim 1, wherein the laser beam emitted from the laser beam illuminating means is a pulsed laser beam.

8. The particle analyzing apparatus according to claim 7, further comprising:

particle detecting means disposed upstream of an illuminated region of the sample liquid being illuminated by the laser beam illuminating means, for detecting at least one of the subject particles; and control means for controlling the laser beam illuminating means to emit the pulsed laser beam after the at least one subject particle has been detected.

9. The particle analyzing apparatus according to claim 1, further comprising gating means disposed between the flow means and the image capturing means, for limiting the laser beam from entering the image capturing means, wherein the laser beam emitted from the laser beam illuminating means is a continuous wave laser beam.

10. The particle analyzing apparatus according to claim 9, further comprising:

particle detecting means for detecting at least one of the subject particles in an illuminated region of the sample liquid being illuminated by the laser beam illuminating means; and control means for causing the image capturing means to capture the image of the at least one subject particle, by controlling the gating means to pass the laser beam to the image capturing means after the at least one subject particle has been detected.

11. The particle analyzing apparatus according to claim 8, wherein the particle detecting means includes judging means for analyzing the detected at least one subject particle to judge whether or not to capture an image of the detected at least one subject particle based on a result of the analysis.

12. The particle analyzing apparatus according to claim 10, wherein the particle detecting means includes judging means for analyzing the detected particle to judge whether to capture an image of the detected particle based on an result of the analysis.

* * * * *